United States Patent [19]

Shionozaki et al.

[11] Patent Number: 4,740,630
[45] Date of Patent: Apr. 26, 1988

[54] CHIRAL PHENYLETHER COMPOUND

[75] Inventors: Yoshio Shionozaki, Nagano; Toshihiro Shibata, Saitama, both of Japan

[73] Assignee: Seiko Epson Corporation, Tokyo, Japan

[21] Appl. No.: 944,636

[22] Filed: Dec. 19, 1986

[30] Foreign Application Priority Data

Dec. 19, 1985 [JP] Japan .................. 60-286322
Oct. 3, 1986 [JP] Japan .................. 61-235854

[51] Int. Cl.$^4$ .......................................... C07C 43/225
[52] U.S. Cl. ..................... 568/656; 568/628
[58] Field of Search ............. 568/630, 647, 628, 656

[56] References Cited

U.S. PATENT DOCUMENTS 4,294,992 10/1981 Hughes ........................... 568/630
4,453,018 6/1984 Nelson ........................... 568/630

OTHER PUBLICATIONS

Shirley et al, J.A.C.S., vol. 73, pp. 458–459 (1951).
Baumann et al, J. Org. Chem., vol. 29, pp. 3055–3057 (1964).

Primary Examiner—James H. Reamer
Attorney, Agent, or Firm—Blum Kaplan

[57] ABSTRACT

A chiral phenylether compound having the formula

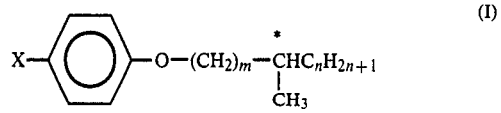

(I)

wherein X is a halogen atom; m is an integer from 3 to 5, n is an integer from 3 to 12 and * designates an asymmetric carbon is disclosed. The chiral phenylether compounds are useful to prepare chiral smectic phase pyrimidine phenylether liquid crystal compounds of the formula.

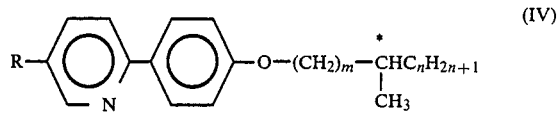

(IV)

The reaction is carried by reacting (I) with butyllithium, dissolving in ether and reacting with a 1-bromoalkane to yield (IV). Compounds (IV) are particularly well suited to broaden the useful temperature range of ferroelectric liquid crystal materials.

9 Claims, No Drawings

CHIRAL PHENYLETHER COMPOUND

BACKGROUND OF THE INVENTION

This invention relates to a chiral phenylether compound and, in particular, to certain specific halogenated phenylether compounds having an alkyl group that includes an asymmetric carbon.

Alkoxybenzene derivatives having asymmetric carbons have recently attracted interest as intermediates of liquid crystal materials. In particular, alkoxybiphenyl compounds, alkoxyphenylpyrimidine compounds, alkoxybenzoic acid derivatives and the like are ferroelectric smectic liquid crystal materials.

The alkoxy group in these liquid crystal compounds is generally 6-methyloctoxy, 2-methylbutoxy and the like. However, these compounds are not suitable for practical use because the temperature range of operation and the stability of the compounds is not satisfactory. Accordingly, extensive studies on ferroelectric liquid crystal compounds have been carried out using this basic skeleton.

Accordingly, it is desirable to provide a ferroelectric smectic liquid crystal material having an asymmetric carbon that is suitable for practical use.

SUMMARY OF THE INVENTION

Generally speaking, in accordance with the invention, a chiral phenylether compound is provided. The compound is represented by the following formula (I) and has excellent optical activity:

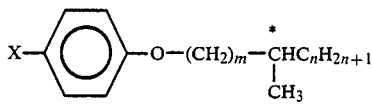

(I)

wherein X represents a halogen atom; m is an integer from 3 to 5, n is an integer from 3 to 12 and * designates the asymmetric carbon. The halogen atom in the compounds is a highly reactivity nuclear substituting group making the compound useful as an intermediate for ferroelectric liquid crystal materials.

Accordingly, it is an object of the invention to provide an improved chiral phenylether compound.

Another object of the invention is to provide a chiral phenylether compound having a halogen atom that is reactive as a nuclear substituting group.

A further object of the invention is to provide a halogenated phenylether compound having an alkyl group and an asymmetric carbon atom that is suitable for practical use as a liquid crystal material.

Still another object of the invention is to provide a chiral phenylether compound that is operative as a ferroelectric liquid crystal material over an acceptable temperature range.

Still a further object of the invention is to provide a stable ferroelectric smectic liquid crystal compound.

Still other objects and advantages of the invention will in part be obvious and will in part be apparent from the specification.

The invention accordingly comprises a composition of matter possessing the characteristics, properties, and the relation of components which will be exemplified in the composition hereinafter described, and the scope of the invention will be indicated in the claims.

DETAILED DESCRIPTION OF THE PREFERRED EMBODIMENTS

The compounds prepared in accordance with the invention have the general formula:

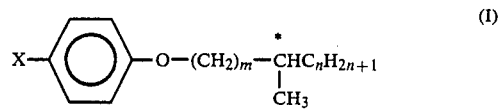

(I)

wherein X represents a halogen atom; m is an integer from 3 to 5; n is an integer from 3 to 12 and * designates the asymmetric carbon. The halogen substituent is highly reactive and functions as a nuclear substituting group. In a preferred embodiment, bromine is used.

The chiral phenylether compound in accordance with the invention is prepared by known etherification techniques. 4-methylalkanol can be converted to the sulfonate and then reacted with 4-halogenated phenol to obtain the phenylether in accordance with the invention.

The invention will be better understood with reference to the following examples. These examples are presented for purposes of illustration only and are not to be construed in a limiting sense.

EXAMPLE 1

Preparation of 4-methyldecyl 4'-bromophenyl ether 172 g (1.0 mol) of 4-methyldecanol and 151.5 g (1.5 mol) of triethylamine were dissolved in 1300 ml of dichloromethane. The mixture was cooled to a temperature of between 0° and −10° C. 149 g (1.3 mol) of methanesulfonyl chloride was added dropwise and the mixture was stirred at the reduced temperature for 2 hours. 1000 ml of dichloromethane was added and the mixture was washed, in sequence, with ice cold water, 10% hydrochloric acid, saturated aqueous sodium carbonate solution and a saturated aqueous salt solution. The mixture was dried with magnesium sulfate. Solvent was removed and the resulting compound was 4-methydecyl methanesulfonate.

A mixture of 125 g (0.5 mol) of the 4-methyldecyl methanesulfonate, 95.1 g (0.55 mol) of 4-bromophenol, 30 g (0.75 mol) of powdered sodium hydroxide and 800 ml of dioxane were mixed and the mixture was stirred under reflux for 8 hours. Gas chromatography was used to confirm the absence of sulfonate. The resulting sodium methanesulfonate was filtered and solvent was removed. The residue was extracted with 1000 ml of toluene and the solution was washed, in sequence, with 5% hydrochloric acid and a saturated aqueous salt solution. Solvent was removed and the residue was distilled under pressure to obtain a distillate of 4-methyldecyl-4'-bromophenyl ether at 165° C. and 1 mmHg.

Infrared spectrum analysis was performed on the resulting 4-methyldecyl-4'-bromophenyl ether and the following results were obtained:

1. Absorption peaks at 1590 and 820 cm$^{-1}$ indicated the presence of the benzene ring;
2. An absorption peak at 1380 cm$^{-1}$ indicated the presence of the methyl group; and
3. A peak at 1250 cm$^{-1}$ indicated the presence of the ether linkage.

These results are consistent with the proposed structure of the compound.

The specific rotary power of the product in a chloroform solvent was $[\alpha]_D = +2.84°$.

EXAMPLE 2

Preparation of 4-methyldodecyl 4'-bromophenyl ether

The same procedure was used as described in Example 1 except that 200 g (1.0 mol) of 4-methyldodecanol was substituted for the 4-methyldecanol. 4-methyldodecyl 4'bromophenyl ether was distilled at 175° C. and 1 mmHg.

The results of infrared spectrum analysis performed on the resulting product were as follows:

1. Absorption peaks at 1590 and 820 cm$^{-1}$ indicated the presence of the benzene ring;
2. An absorption peak at 1380 cm$^{-1}$ indicated the presence of a methyl group; and
3. A peak at 1250 cm$^{-1}$ indicated the presence of the ether linkage.

These results are consistant with the proposed structure of the compound.

The specific rotary power of the product in a chloroform solvent was $[\alpha]_D = +1.99°$.

EXAMPLE 3

Preparation of 6-methyldecyl 4'bromophenyl ether 51.7 g (0.3 mol) of 6-methyl-1-decanol having a specific rotary power of a 1.612% chloroform solution at 27° C. of $[\alpha]_D = -0.62°$, 62.9 g (0.33 mol) of paratoluenesulfonylchloride, and 36.4 g (0.36 mol) of triethylamine were dissolved in toluene and tosylation was performed by a known method to obtain 92.1 g of paratoluenesulfonate.

6.53 g (0.02 mol) of the paratoluenesulfonate (an ester sulfonate) and 5.19 g (0.03 mol) of 4-bromophenol were homogeneously dissolved in 30 ml of dioxane. 1.6 g (0.04 mol) of powdered sodium hydroxide was added and the mixture was reacted under reflux for 3 hours. The reaction product was extracted with 100 ml of toluene and washed, in sequence, with a 5% aqueous solution of caustic soda, a 5% aqueous solution of hydrochloric acid and a saturated aqueous solution of sodium chloride. The solution was dried and solvent was removed. 6.18 g of a yellowish transparent liquid was obtained and the purity of the primary constituent was 94.8% as measured by gas chromatography. The solution was diluted with hexane used as a developing solvent and the developed solution was purified using a silica gel column. The purified solution was distilled by the Kugel rohl method to obtain 4-methyldecyl 4'-bromophenyl ether having a boiling point of between 138° and 141° C. at a pressure of 0.5 mmHg.

Infrared spectrum analysis showed the following characteristic absorption peaks:

1. Peaks at 1595, 1490 and 825 cm$^{-1}$ indicated the presence of the benzene ring;
2. A peak at 1380 cm$^{-1}$ indicated the methyl group; and
3. A peak at 1250 cm$^{-1}$ indicated the presence of the ether linkage.
4. The specific rotary power of the product in a 1.538% chloroform solution at 26° C. was $[\alpha]_D = -0.39°$.

EXAMPLE 4

Preparation of 6-methylnonyl 4'bromophenyl ether

The method described in Example 3 was followed except that 6-methyl-1-nonanol was substituted for the 6-methyl-1-decanol. The 6-methyl-1-nonanol had a specific rotary power in a 1.432% chloroform solution at 28° C. of $[\alpha]_D = +1.67°$. 6-methylnonyl 4'-bromophenyl ether was obtained by distillation at a boiling point of 165° C. under pressure of 0.15 mmHg.

The results of infrared spectrum analysis show characteristic absorption peaks as follows:

1. Peaks at 1595 and 820 cm$^{-1}$ indicated the presence of a benzene ring;
2. A peak at 1380 cm$^{-1}$ indicated the presence of the methyl group; and
3. A peak at 1250 cm$^{-1}$ indicated the presence of an ether linkage.
4. The specific rotary power of a 1.412% chloroform solution of the product at 26° C. was $[\alpha]_D = +0.85°$.

EXAMPLE 5

Preparation of 5-methyltridecyl 4'-bromophenyl ether

1. Preparation of 5-methyltridecanol 2 g of magnesium shavings were dispersed in 8 m of anhydrous ether in an argon stream. 4 g of 4-methyl-1-dodecylbromide dissolved in 4 ml of anhydrous ether was added dropwise in order to prepare the Grignard reagent. Gaseous formaldehyde was injected into the Grignard reagent at room temperature for 90 minutes and the solution was cooled to 0° C. 20 ml of ice cold water and 6 ml of concentrated sulfuric acid were added and precipitates were completely dissolved. The organic layer was washed with 5% hydrochloric acid and solvent was removed.

10 ml of ethanol and 0.4 ml of concentrated hydrochloric acid were added to the residue and the mixture was refluxed for 4 hours. Solvent was removed and the resulting product was extracted with benzene. The crude product was distilled using the method of Kugel rohl and the distillate was obtained at a boiling point of between 112° and 114° C. at a pressure of 0.25 mmHg. The distillate was diluted with a hexane/ethyl acetate mixture solution as a developer in a ratio of 85 parts hexane to 15 parts ethyl acetate and purified using a silica gel column. 5-methyltridecanol having a purity of 97.3% was obtained.

2. Preparation of phenyl ether

The 5-methyltridecanol was used in the method described in Example 3. The distillate was obtained at a boiling point of between 150° and 151° C. at a pressure of 0.2 mmHg. The distillate was diluted with hexane as a developing solvent and purified using a silica gel column to obtain 5-methyltridecyl 4'-bromophenyl ether.

Infrared spectrum analysis showed the following characteristic absorption peaks;

1. Peaks at 1595 and 820 cm$^{-1}$ indicated the presence of a benzene ring;
2. A peak at 1380 cm$^{-1}$ indicated the presence of the methyl group; and
3. A peak at 1250 cm$^{-1}$ indicated the presence of an ether linkage.
4. The specific rotary power of a 1.512% chloroform solution of the product at 29° C. was $[\alpha]_D = -0.206°$.

The chiral phenyether compounds prepared in accordance with the invention may be used as intermediates to form 2-phenylpyridine compounds represented by the general formula

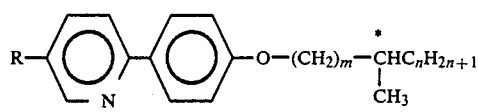

These 2-phenylpyridine compounds have a chiral smectic phase C ("SmC*"). It s generally known that ferroelectric liquid crystal materials exhibit SmC* and have electro-optical switching properties and memory properties that are better than those of any other compounds known in the prior art as discussed in N. A. Clark et al, *Applied Physics Letters*, Vol. 36, p. 899 (1980).

The 2-phenylpyridine compounds represented by formula (IV) are particularly well suited for practical use since they can be used over a wide temperature range from extremely low temperatures to relatively high temperatures. For example, compounds 6 and 7, shown in Table 1 below, show SmC* at extremely low temperatures, specifically, from 36.4° to −2.7° C. and from 46.8° to 4.1° C., respectively. On the other hand, compounds 11 and 15 are useful at relatively high temperatures, from 70.6° to 58.5° C. and from 73.0° to 50.5° C., respectively. The temperature ranges can be arbitrarily selected by changing the position of the asymmetric carbon of the intermediates of formula (I). Specifically, the temperature characteristics of the final liquid crystal material is dependent on the arrangement of m and n.

The 2-phenylpyridine compounds represented by formula (IV) can be prpared using the phenylether compounds (I) by the following process.

[Reaction Process]

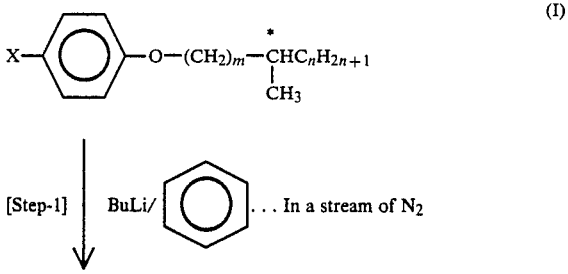

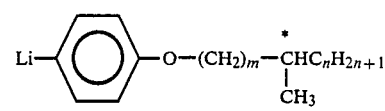

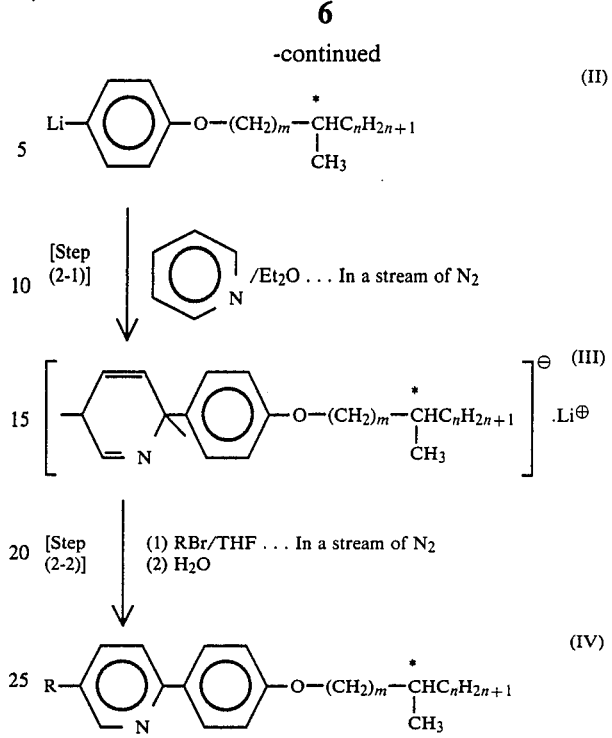

The chiral phenylether compounds prepared in accordance with the invention are reacted with butylithium in benzene in a stream of nitrogen to obtain the lithium phenylether compound represented by formula (II). Compound (II) is reacted with pyridine in ethyl ether to obtain the phenylpyridine lithium compound represented by the formula (III) which is dissolved in the ether solution. Tetrahydrofuran and 1-bromoalkane are added and the reaction is allowed to occur and the reaction mixture is hydrolyzed to obtain the 2-phenylpyridine compound represented by formula (IV).

The following 2-phenylpyridine compounds (IV) shown in Table 1 were prepared from the chiral phenyl ether components (I): utilizing this procedure.

TABLE 1

| COMPOUND NO. | COMPOUND (IV) $C_nH_{2n+1}$ | R | m | PHASE TRANSITION TEMPERATURE (°C.) K | Smx | Smy | SmC* | SmA | Ch | Iso |
|---|---|---|---|---|---|---|---|---|---|---|
| 1 | $C_3H_7$ | $C_9H_{19}$ | 3 | ·42.3 (33.8·) | ·58.0 (47.7·) |  | ·64.4 (60.5·) | — | — | · |
| 2 | $C_3H_7$ | $C_{11}H_{23}$ | 3 | ·36.2 (20.5·) | ·55.6 (43.0·) |  | ·58.7 (52.6·) | — | — | · |
| 3 | $C_4H_9$ | $C_{10}H_{21}$ | 3 | ·62.2 (33.5·) (40.5·) | — |  | (57.2·) | — | — | · |
| 4 | $C_5H_{11}$ | $C_8H_{17}$ | 3 | ·35.0 (11.6·) (46.5·) | ·47.1 |  | ·62.4 (58.5·) | — | — | · |
| 5 | $C_5H_{11}$ | $C_9H_{19}$ | 3 | ·26.6 (0.4·) (39.0·) | ·39.9 | — | ·55.1 (54.6·) |  | — | · |
| 6 | $C_5H_{11}$ | $C_{10}H_{21}$ | 3 | ·35.3 (−2.7·) | ·54.7 | — | (36.4·) | — | — | · |
| 7 | $C_6H_{13}$ | $C_8H_{17}$ | 3 | ·50.0 (−15.4·) (4.1·) | — |  | (46.8·) | — | — | · |
| 8 | $C_6H_{13}$ | $C_{12}H_{25}$ | 3 | ·50.7 (28·) (38.6·) | ·54.8 | — | (51.7·) | — | — | · |
| 9 | $C_8H_{17}$ | $C_8H_{17}$ | 3 | ·48.2 (−6.6·) (27.3·) | — |  | (43.3·) | — | — | · |
| 10 | $C_8H_{17}$ | $C_9H_{19}$ | 3 | ·42.2 (−1.4·) (34.5·) | ·50.1 | — | (48.4·) |  | — | · |
| 11 | $C_8H_{17}$ | $C_{12}H_{25}$ | 3 | ·45.0 (38.0·) (58.5·) | ·59.0 | — | ·71.5 (70.6·) | — | — | · |

TABLE 1-continued

| COMPOUND NO. | COMPOUND (IV) $C_nH_{2n+1}$ | R | m | PHASE TRANSITION TEMPERATURE (°C.) K | Smx | Smy | SmC* | SmA | Ch | Iso |
|---|---|---|---|---|---|---|---|---|---|---|
| 12 | $C_3H_7$ | $C_7H_{15}$ | 5 | ·30.5 (0.2·) | ·42.5 (36.3·) |  | ·56.0 (53.2·) | — | — | · |
| 13 | $C_3H_7$ | $C_9H_{19}$ | 5 | ·33.0 (8.1·) | ·52.2 (51.9·) | — | ·68.1 | — | — | · |
| 14 | $C_3H_7$ | $C_{11}H_{23}$ | 5 | ·28.4 (−4.0·) | ·65 (17.5·) | (36.8·) | (47.0·) | — | — | · |
| 15 | $C_4H_9$ | $C_7H_{15}$ | 5 | ·43.4 (28.6·) | ·59.8 | (50.5·) | ·73.5 (73.0·) | — | — | · |
| 16 | $C_4H_9$ | $C_9H_{19}$ | 5 | ·37.2 (12.0·) | ·56.8 (51.4·) | (60.4·) | ·63.7 | — | — | · |
| 17 | $C_4H_9$ | $C_{11}H_{23}$ | 5 | ·26.6 (11.5·) | ·45.1 (32.0·) | — | ·58.9 (54.7·) | ·71.2 (68.7·) | — | · |

In Table 1, K represents the crystalline phase, Smx and Smy are unidentified smectic phases, SmA is Smectic phase A, Ch is a cholesteric phase, and Iso is an isotropic liquid phase. The figures in parenthesis refer to the monotropic phase transition. A period (".") means that the compound presents such a phase, and a dash ("-") means that the compound does not present such a phase.

The pyridine phenylether compound No. 8 was mixed with a ferroelectric liquid crystal compound to prepare the composition shown in Table 2. The composition of Table 2 was thermally sealed into a space between two glass substrates that had a rubbed surface and transparent electrodes thereon. The substrates formed an electro-optic element having a thickness of between about 1 and 2 μm and the element was sandwiched between a polarizer and an analyzer with the axis perpendicular to each other. An alternating electric field of ±12 volts was applied across the electrodes. As a result, the liquid crystal composition responded in accordance with the direction of the electric field.

TABLE 2

| COMPOUND | COMPOSITION RATE (wt %) |
|---|---|
| ferroelectric liquid crystal compound CS-1000 (made by Chisso Corporation) | 70 |
| $C_6H_{13}*CH(CH_2)_3O$—⟨ring⟩—⟨ring-N⟩—$C_{12}H_{25}$ <br> \|  <br> $CH_3$ <br> (compound No. 8) | 20 |
| $C_8H_{17}$—⟨ring⟩—⟨ring⟩—COO—⟨ring⟩—$CH_2*CHC_2H_5$ <br> \| <br> $CH_3$ | 10 |

| PHASE TRANSITION POINT (°C.) | SmC* | SmA | Ch | Iso |
|---|---|---|---|---|
|  | 58 | 71 | 77 |  |

The transition point from SmA to SmC* was relatively high, specifically 58° C. In addition, the SmC* temperature was wide. Around room temperature (25° C.) the operation temperature range was good at about ±5°. Contrast was also very good, i.e. 1:10 in the same temperature range. In addition, the Im/Ip ratio, the ratio of the light transmittance Im when the electric field was removed, that is when memory was operated, over the light transmittance Ip when the electric field was applied was greater than 0.9. Accordingly, memory properties were good.

Ferroelectric liquid crystal compositions prepared using the compounds prepared in accordance with the invention have extremely wide drive and temperature ranges, good contrast and very good memory properties even when the cell thickness is about 1 to 2 μm. Such compounds can be used in light liquid crystal shutters or high multiplex liquid crystal displays and the like. The phenylpyridine compounds may be incorporated into the ferroelectric liquid crystal composition in an effective amount to vary the useful temperature range as desired. For example, they may be included in an amount from about 10 to 30 weight percent based on the total weight of the composition.

Accordingly, a chiral phenylether compound having a halogen atom that is highly reactivity and useful as a nuclear substituting group, an alkyl group and an asymmetric carbon is obtained. The compounds have excellent optical activity, are stable and can be used to prepare compounds that are suitable for use over the required temperature range.

A "ferroelectric liquid crystal material" as used herein is a liquid crystal material which exhibits ferroelectric properties as follows.

When an electric field is applied to a dielectric liquid crystal having permanent dipoles, the dipoles are oriented with the direction of the applied electric field and dielectric polarization occurs. When electrostatic interaction between permanent dipoles is strong, the dipoles are arranged in parallel even without application of the external electric field. When dipoles are arranged in parallel, spontaneous polarization exists. The property that the direction of this spontaneous polarization can be reversed by externally applying an electric field is known as "ferroelectricity", and a liquid crystal material having this property is a "ferroelectric liquid crystal material".

It will thus be seen that the objects set forth, among these made apparent from the preceding description, are efficiently attained and, since certain changes may be made in the above product without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall there between.

Particularly it is to be understood that in the claims, ingredients or compounds recited in the singular are intended to include compatible mixtures of such ingredients wherever the sense permits.

What is claimed is:

1. A chiral phenylether compound represented by the formula (I):

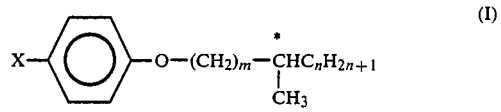

wherein X represents a halogen atom; m is an integer from 3 to 5, n is an integer from 3 to 12 and * designates an asymmetric carbon.

2. The chiral phenylether compound of claim 1, wherein X is selected from the group consisting of chlorine, bromine, iodine and fluorine.

3. The chiral phenylether compound of claim 2, wherein X is bromine.

4. The chiral phenylether compound of claim 1, wherein n is between 4 and 10.

5. The chiral phenylether compound of claim 1, wherein the compound is 4-methyldecyl 4'-bromophenyl ether.

6. The chiral phenylether compound of claim 1, wherein the compound is 4-methyldodecyl 4'-bromophenyl ether.

7. The chiral phenylether compound of claim 1, wherein the compound is 6-methyldecyl 4'-bromophenyl ether.

8. The chiral phenylether compound of claim 1, wherein the compound is 6-methylnonyl 4'-bromophenyl ether.

9. The chiral phenylether compound of claim 1, wherein the compound is 5-methyltridecyl 4'-bromophenyl ether.

* * * * *